United States Patent [19]
Atsumi

[11] Patent Number: 5,588,966
[45] Date of Patent: Dec. 31, 1996

[54] DEVICE FOR REMOVING A NEEDLE FROM A SYRINGE

[75] Inventor: Haruo Atsumi, Shizuoka-ken, Japan

[73] Assignee: A.C.E. Corporation, Shizuoka-ken, Japan

[21] Appl. No.: 502,309

[22] Filed: Jul. 13, 1995

[30]   Foreign Application Priority Data

Jul. 25, 1994  [JP]  Japan .................................. 6-192798

[51] Int. Cl.⁶ ............................................................ A61M 5/00
[52] U.S. Cl. ................................................................ 604/110
[58] Field of Search ............................... 604/110, 192, 604/187, 263; 206/365, 366

[56]           References Cited

U.S. PATENT DOCUMENTS

| 4,986,811 | 1/1991 | Thead et al. | 604/110 |
| 5,069,667 | 12/1991 | Freundlich et al. | 604/110 |
| 5,356,385 | 10/1994 | Latini | 604/110 |

FOREIGN PATENT DOCUMENTS

| 2213038 | 3/1992 | Japan . | |
| 3210441 | 9/1992 | Japan . | |
| 5269174 | 10/1993 | Japan | 604/110 |

Primary Examiner—John D. Yasko
Attorney, Agent, or Firm—Harrison & Egbert

[57]           ABSTRACT

A device which makes it possible to remove a needle from a syringe very easily and safely. The device comprises a supporter, a syringe barrel receiver attached to the supporter slidably in the axial direction of the syringe, a rotatable member or members having a needle remover for removing the needle from the syringe, the rotatable member or members being attached to the supporter rotatably in the direction of removing the needle from the syringe, the rotatable member or members further having a spring for keeping the rotatable member or members in contact with a portion of the syringe barrel receiver and for returning the rotatable member or members and the syringe barrel receiver respectively to their original positions.

4 Claims, 8 Drawing Sheets

DEVICE FOR REMOVING A NEEDLE FROM A SYRINGE

BACKGROUND OF THE INVENTION (1) Field of the Invention

The present invention relates to a device for removing a needle from a syringe. In the specification and claims, the syringe is a device by means of which fluids are injected into, or extracted from, the human body.

(2) Description of the Prior Art

To prevent doctors and nurses from being infected with AIDS, hepatitis B, etc. within the hospital, in recent years syringes including the barrel and the needle are discarded after use and used syringes are to be never used again. Therefore, a great number of used syringes are being discarded. To prevent people who handle used syringes outside the hospital from being infected with AIDS, hepatitis B, etc., when used syringes are discarded in the hospital, the needle is removed from the barrel and put into a container designed for containing used needles or the needle is covered with a sheath, removed from the barrel and discarded along with the barrel.

However, it is troublesome to remove the needle from the barrel by hand and put the needle into the container. Furthermore, there is the risk of the fingers, etc. being pricked with the needle in removing the needle from the barrel or putting the needle into the container. Particularly at the time of covering the needle with a sheath, the fingers, etc. are often pricked with the needle. If the fingers, etc. are priced with a used needle, the person may be infected with AIDS, hepatitis B, etc.

In view of the above, Japanese Patent Laid-Open Publication No. Hei 4-244167 provides an improved needle sheath. Japanese Patent Laid-Open Publication No. Hei 4-96763 provides a device for removing a needle from the barrel of a syringe and putting the needle into a container. The device of said Japanese Patent Laid-Open Publication No. Hei 4-96763 comprises a needle container, a needle removing slit provided on the top of said needle container, a needle guide provided on the opposite sides of said needle removing slit, said needle guide being adapted to be inserted between the end surface of the barrel and the hub or head of the needle, said needle guide being tapered from one end of said needle removing slit to the other end thereof. In this device, the needle of a syringe is removed from the barrel thereof by putting the needle into the needle removing slit so that the needle guide is inserted between the end surface of the barrel and the hub or head of the needle, and then inclining said barrel.

However, the prior art has disadvantages as follows:

Said Japanese Patent Laid-Open Publication No. Hei 4-244167 only discloses said needle sheath. Even if the needle is covered with said sheath, it is still necessary to remove the needle from the barrel of the syringe.

The device of said Japanese Patent Laid-Open Publication No. Hei 4-96763 requires actions such as elaborately inserting said needle guide between tile end surface of the barrel and the hub or head of the needle and inclining said barrel of the syringe. Such actions are very troublesome and unsuitable for hospital business which demands haste.

SUMMARY OF THE INVENTION

It is therefore an object of the invention to provide a device for removing a needle from a syringe, which device has obviated all the disadvantages of the prior art.

It is another object of the invention to provide a device for removing a needle from a syringe, by means of which device the needle can be removed from the syringe very easily.

It is a further object of the invention to provide a device for removing a needle from a syringe, by means of which device the needle can be removed from the syringe very safely.

These and other objects have been attained by a device for removing a needle from a syringe, comprising a supporting means, a syringe barrel receiving means attached to said supporting means slidably in the axial direction of the syringe, a rotatable member or members having a needle removing means for removing the needle from the syringe, said rotatable member or members being attached to said supporting means rotatably in the direction of removing the needle from the syringe, said rotatable member or members further having a spring means for keeping said rotatable member or members in contact with a portion of said syringe barrel receiving means and for returning said rotatable member or members and said syringe barrel receiving means respectively to their original positions.

The distance between the position in which said portion of said syringe barrel receiving means contacts said rotatable member and a supporting shaft of said rotatable member is preferably shorter than the distance between said needle removing means of said rotatable member and said supporting shaft of said rotatable member.

Said needle removing means of said rotatable member or members preferably has elasticity.

The operation of the device for removing a needle from a syringe according to the present invention will now be described.

A needle can be removed from a used syringe simply by pressing an end of the syringe barrel having the needle against said syringe barrel receiving means. Then, the syringe barrel receiving means slides in the axial direction of the syringe and said portion of the syringe barrel receiving means turns said rotatable member or members, against the force of said spring means, in the direction of removing the needle from the syringe. Now, said needle removing means of the rotatable member or members removes the needle from the syringe barrel by moving the needle in the direction of separating the needle from the syringe barrel. When the syringe barrel is moved away from the syringe barrel receiving means after the needle is removed from the syringe barrel, said spring means of the rotatable member or members returns the rotatable member or members and the syringe barrel receiving means respectively to their original positions.

Since the distance between the position in which said portion of said syringe barrel receiving means contacts said rotatable member and a supporting shaft of said rotatable member is shorter than the distance between said needle removing means of said rotatable member and said supporting shaft of said rotatable member, the distance for which said portion of the syringe barrel receiving means moves is shorter than the distance for which said needle removing means moves. In other words, the distance for which said needle removing means moves is longer than the distance for which said portion of the syringe barrel receiving means moves. Therefore, the needle removing means of the rotatable member or members surely removes the needle from the syringe barrel.

Since said needle removing means of said rotatable member or members has elasticity, the needle removing means grasps the needle with a suitable force when the rotatable member or members is rotated in the direction of removing the needle from the syringe. Therefore, the needle removing means surely contacts the needle and smoothly separates the needle from the syringe barrel without damaging or destroying the needle.

DETAILED DESCRIPTION OF THE PRESENT INVENTION

The present invention will now be described in detail with reference to the attached drawings.

Figure 7:
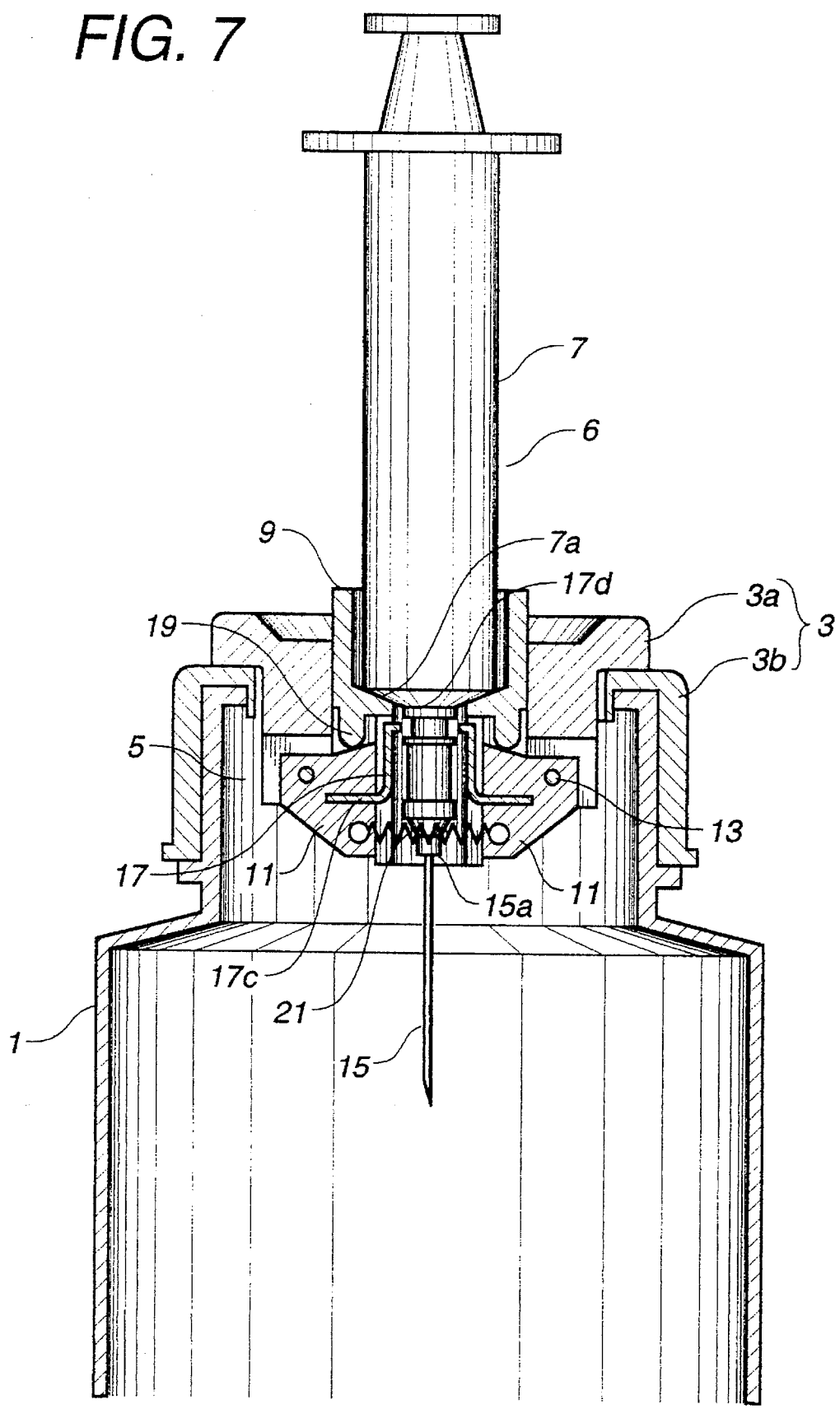
FIG. 7 is a sectional view showing another example of the device for removing a needle from a syringe according to the present invention.
Figure 8:
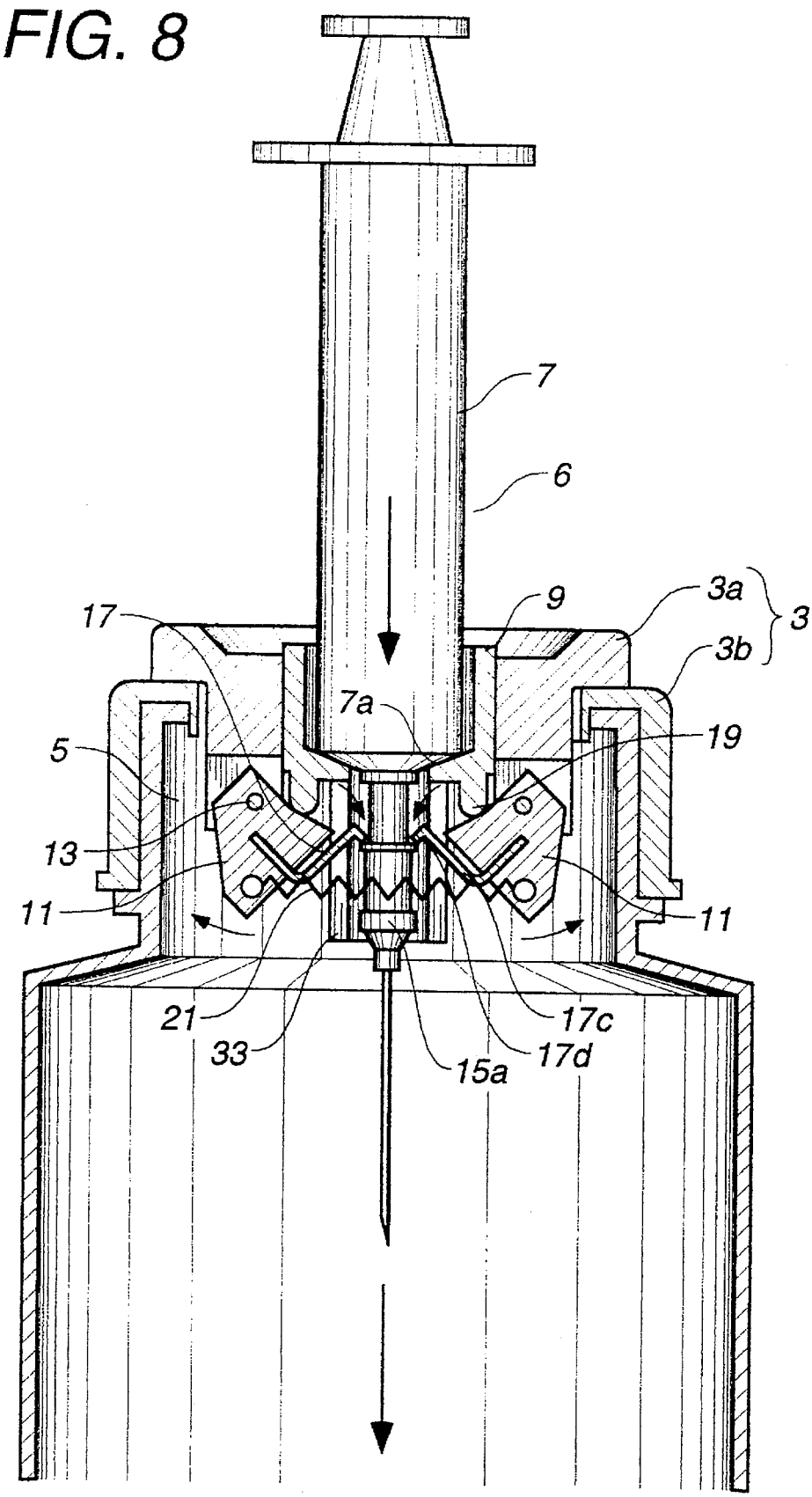
FIG. 8 is a sectional view showing said device in which an end of a syringe barrel is pressed against a syringe barrel receiving means.

In FIGS. 1, 2, 7 and 8, numeral 1 represents a container for containing removed needles. The container 1 is provided with a cap 3 which serves as a supporting means. The supporting means 3 may be detachably attached to an opening 5 of the container 1. For example, the supporting means 3 may be in threaded engagement with the opening 5 of the container 1. In FIGS. 7 and 8, the supporting means 3 comprises two component members 3a and 3b fastened together. A syringe barrel receiving means 9 for receiving a barrel 7 of a syringe 6 is attached to said supporting means 3 slidably in the axial direction of the syringe 6. The syringe barrel receiving means 9 receives an end 7a of the syringe barrel 7, at which end a needle 15 is attached.

In the drawings, two rotatable members 11, each having a needle removing means 17 for removing the needle 15 from the syringe 6, are attached to said supporting means 3 rotatably in the direction of removing the needle 15 from the syringe 6. Numeral 13 represents a supporting shaft on which the rotatable member 11 turns. The rotatable members 11 have a spring means 21 for keeping each of the rotatable members 11 in contact with a portion 19 of said syringe barrel receiving means 9 and for returning the rotatable members 11 and the syringe barrel receiving means 9 respectively to their original positions.

Said needle removing means 17 of the rotatable members 11 preferably has elasticity. The needle removing means 17 may be any of the following for example:

(1) A needle removing means 17 comprising an arm portion 17a integrally protruding from said rotatable member 11, said arm portion 17a being provided at its end with an engagement catch 17b. See FIGS. 1 and 2. In this example, the needle removing means 17 is made of a synthetic resin integrally with the rotatable member 11 so that the needle removing means 17 has elasticity. The engagement catch 17b of the arm portion 17a is adapted to be engaged with a hub or head 15a of the needle 15.

(2) A needle removing means 17 comprising an arm portion 17c fixed to the rotatable member 11, said arm portion 17c being provided at its end with an engagement catch 17d. See FIGS. 7 and 8. In this example, the arm portion 17c is made of an elastic material so that the needle removing means 17 has elasticity. The engagement catch 17d of the arm portion 17c is adapted to be engaged with the hub or head 15a of the needle 15.

Figure 9:
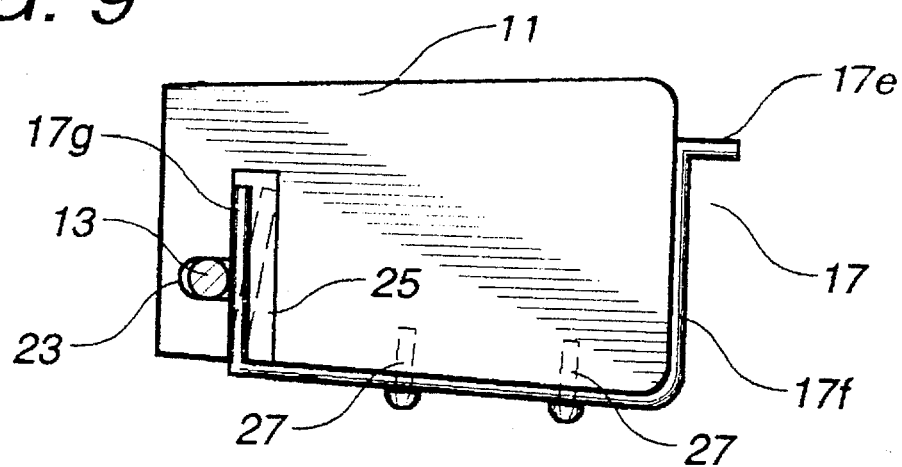
FIG. 9 is a side view showing a modified example of a needle removing means.

(3) A needle removing means 17 comprising an arm portion 17f fixed to the rotatable member 11, said arm portion 17f being provided at its end with an engagement catch 17e, said arm portion 17f and said rotatable member 11 being movable with respect to the supporting shaft 13. See FIG. 9. An elongated hole 23 is made in the rotatable member 11. The supporting shaft 13 of the rotatable member 11 is inserted into the elongated hole 23. A cut 25 is further made in the rotatable member 11 so as to be connected to said elongated hole 23. The arm portion 17f provided at its end with the engagement catch 17e is fixed to the rotatable member 11 by means of screws 27. A base portion 17g of the arm portion 17f is movably inserted into said cut 25. In this example, elasticity is given to the needle removing means 17 by forming the arm portion 17f of an elastic material and making the base portion 17g of the arm portion 17f movable within the cut 25. In FIG. 9, when the engagement catch 17e of the arm portion 17f engages with the hub or head 15a of the needle 15 and receives a force in the leftward direction thereby, then the rotatable member 11 is moved toward the left with respect to the supporting shaft 13, and the base portion 17g of the arm portion 17f made of an elastic material is pushed toward the right by the supporting shaft 13 and bent toward the right within the cut 25.

Figure 11:
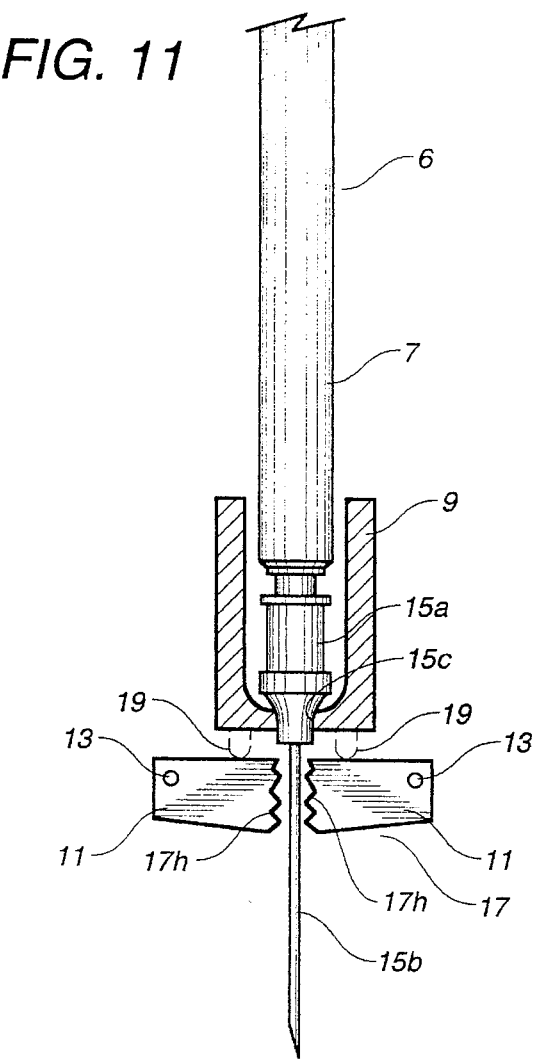
FIG. 11 is a sectional view schematically illustrating a further example of the device for removing a needle from a syringe according to the present invention.

(4) A needle removing means 17 comprising rotatable members 11 disposed on the opposite sides of a needle cannula 15b, each of said rotatable members 11 being provided on its end facing the needle cannula 15b with engagement teeth 17h. See FIG. 11. In this example, the engagement teeth 17h of the rotatable members 11 hold the needle cannula 15b of the needle 15 between them and remove the needle cannula 15b from the hub or head 15a of the needle 15 as the rotatable members 11 are turned through the mechanism mentioned above.

Figure 12:
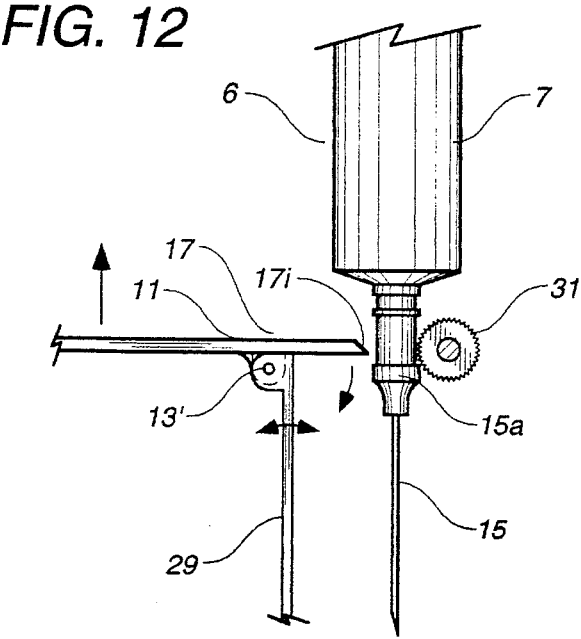
FIG. 12 is a side view showing a modified example of a rotatable member.

(5) A needle removing means 17 comprising an elastic member 29 fixed to the supporting means 3, a rotatable member 11 attached to said elastic member 29 rotatably in the direction of removing the needle 15 from the syringe 6, said rotatable member 11 being provided at its end with an engagement catch 17i. See FIG. 12. Reference symbol 13' represents a shaft of the rotatable member 11. The rotatable member 11 may be disposed on each of the opposite sides of the needle 15. In FIG. 12, the rotatable member 11 is disposed on one side of the needle 15 and a gear 31 is disposed on an opposing side of the needle 15. In FIG. 12, the engagement catch 17i of the rotatable member 11 contacts and moves down the hub or head 15a of the needle 15 as the rotatable member 11 is turned through the mechanism mentioned above. At this time, the hub or head 15a of tile needle 15 is held between the engagement catch 17i of the rotatable member 11 and the gear 31. In this example, elasticity is given to the needle removing means 17 by attaching the rotatable member 11 to the elastic member 29 fixed to the supporting means 3.

Figure 1:
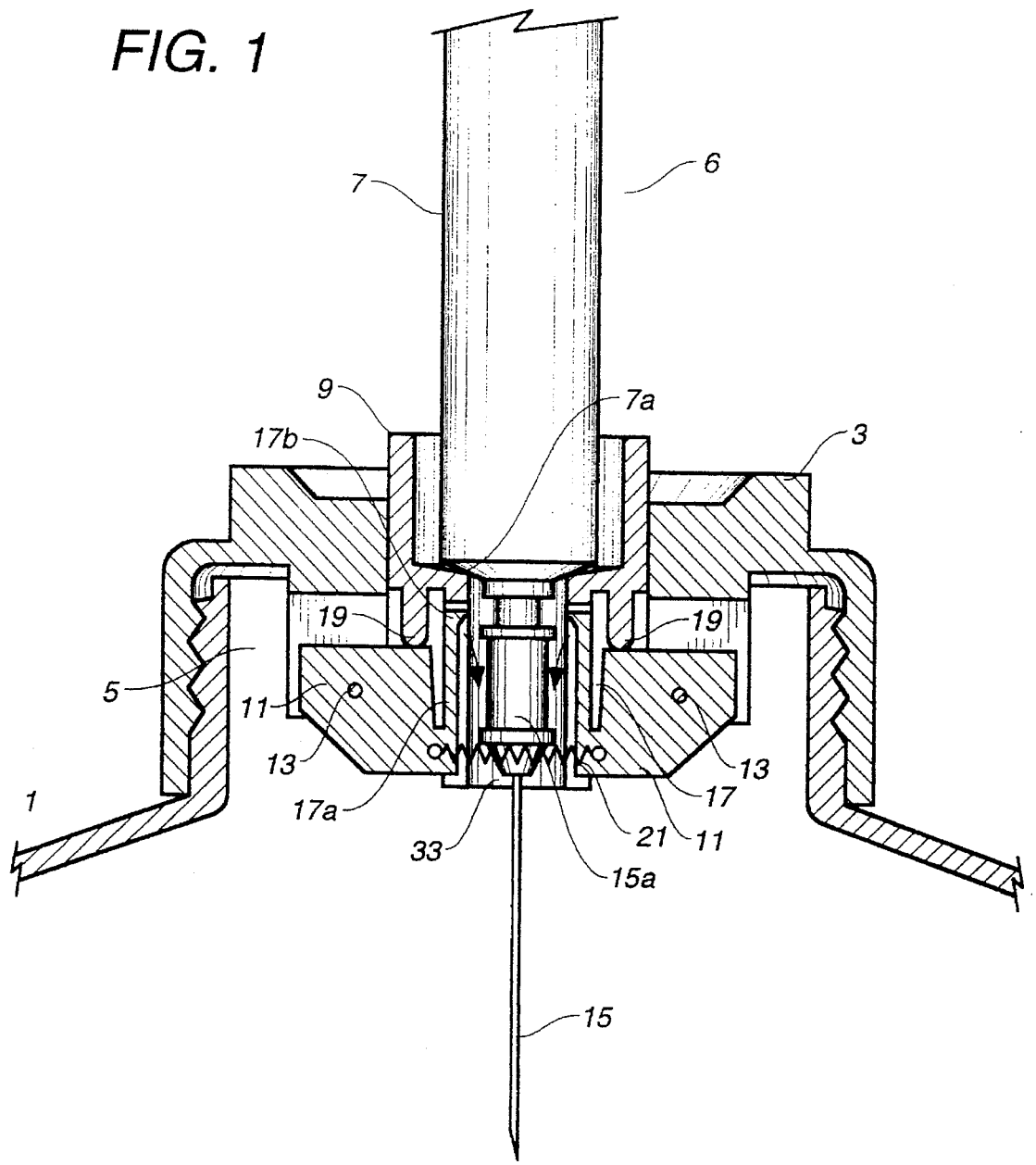
FIG. 1 is a sectional view showing an example of a device for removing a needle from a syringe according to the present invention.
Figure 2:
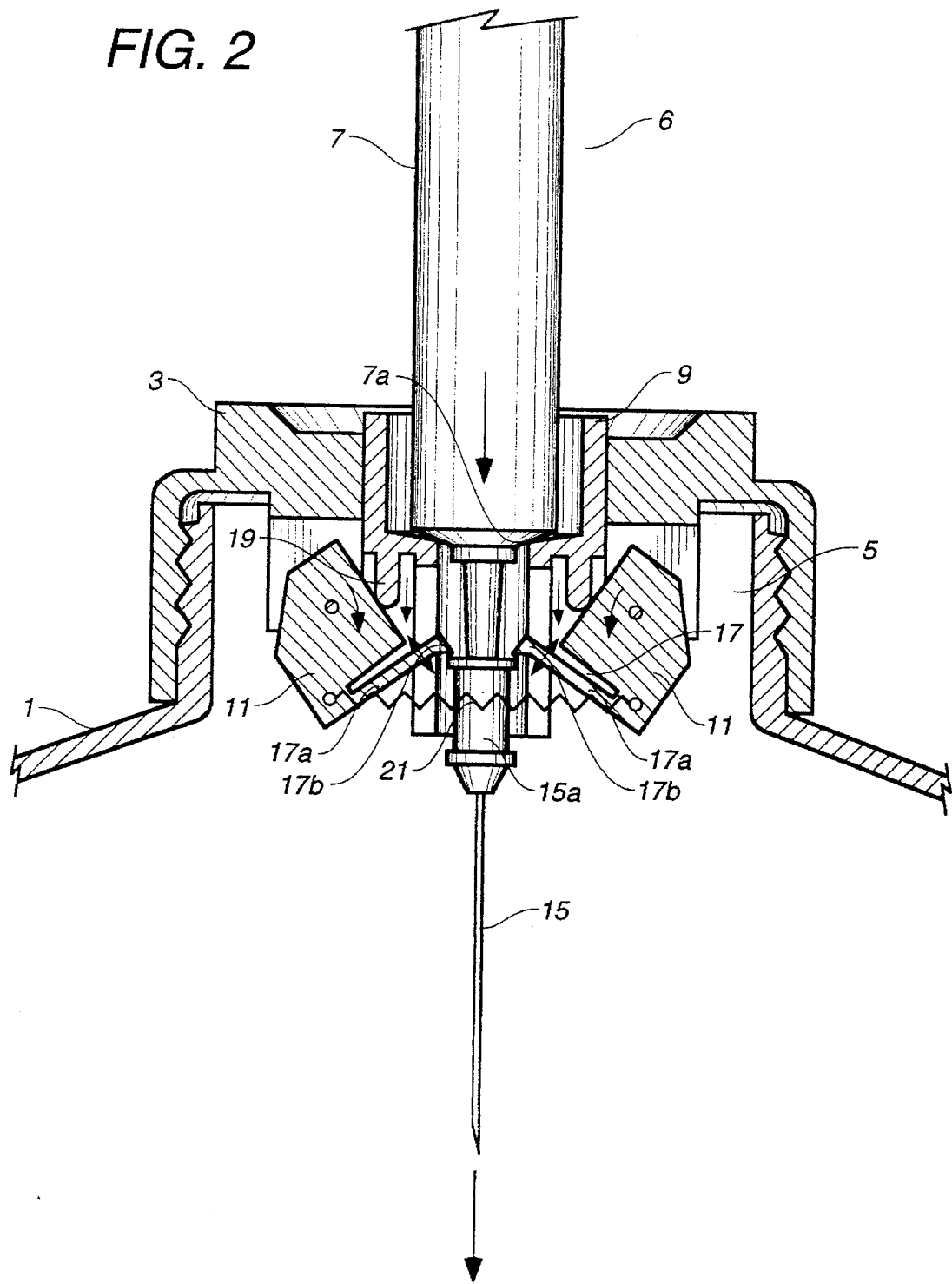
FIG. 2 is a sectional view showing said device in which an end of a syringe barrel is pressed against a syringe barrel receiving means.

The distance between tile position in which the above-mentioned portion 19 of the syringe barrel receiving means 9 contacts the rotatable member 11 and the supporting shaft 13 of the rotatable member 11 is preferably shorter than the distance between the needle removing means 17 of the rotatable member 11 and the supporting shaft 13 of the rotatable member 11. As shown in FIGS. 1 and 2, for example, the portion 19 of the syringe barrel receiving means 9 preferably contacts the rotatable member 11 in a position between the needle removing means 17 and the supporting shaft 13.

Figure 3:
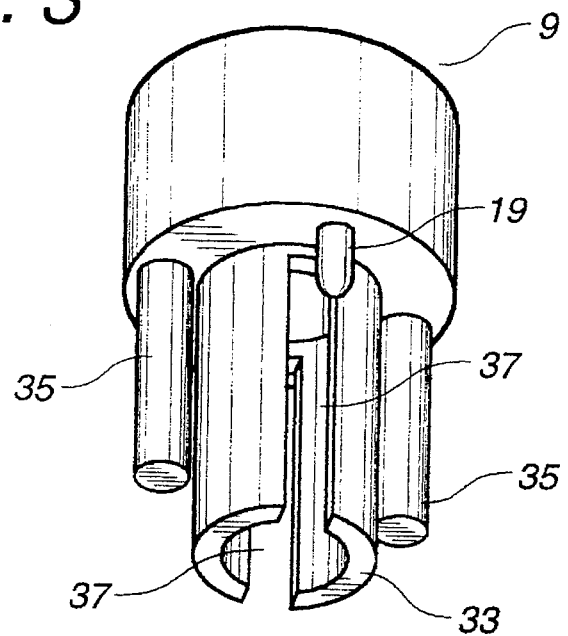
FIG. 3 is a perspective view showing said syringe barrel receiving means.
Figure 4:
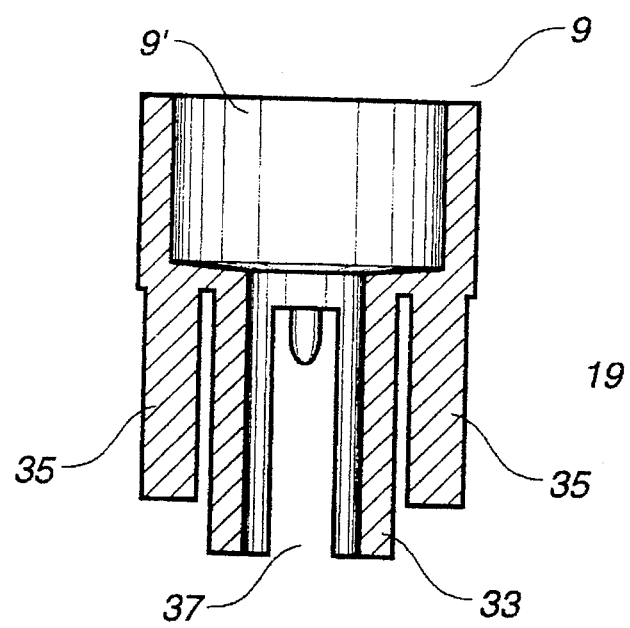
FIG. 4 is a sectional view showing said syringe barrel receiving means.
Figure 5:
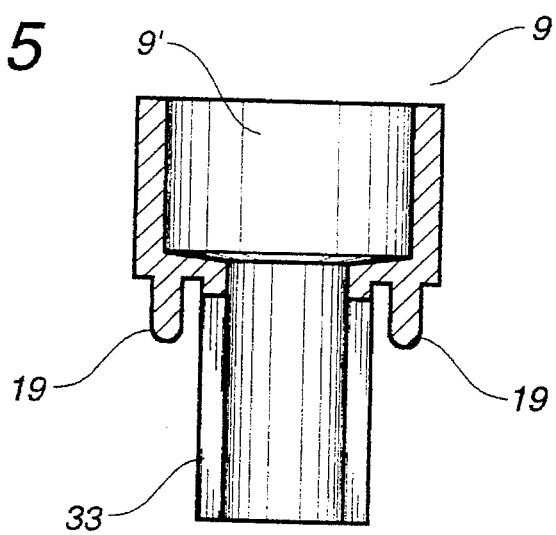
FIG. 5 is another sectional view showing said syringe barrel receiving means.
Figure 6:
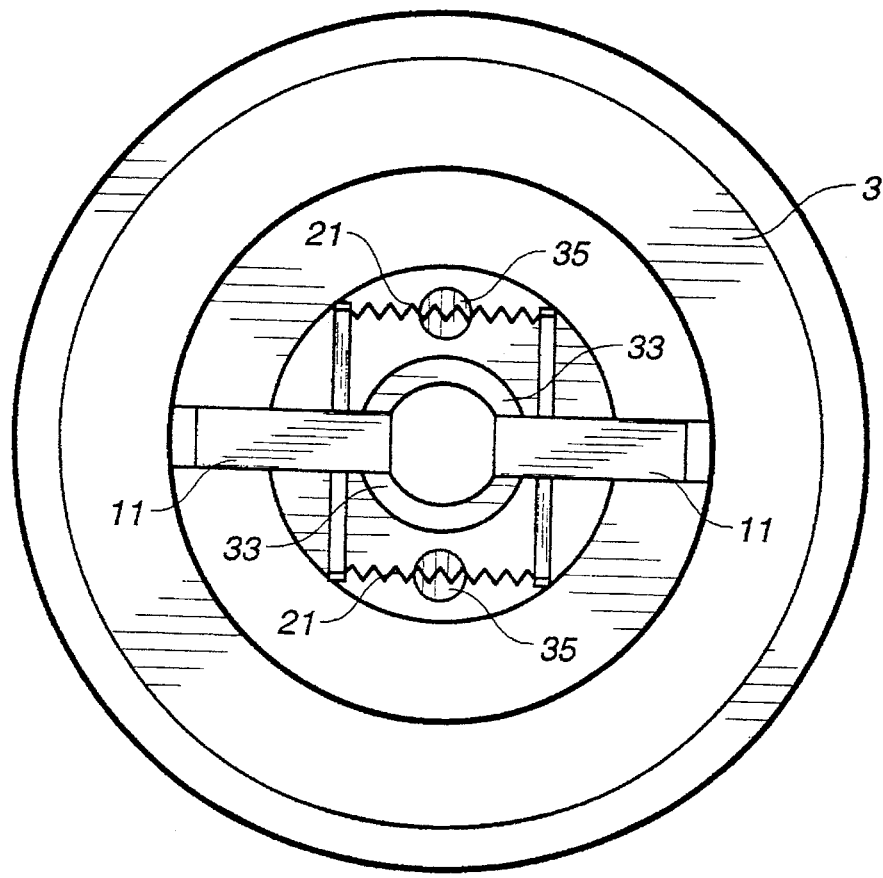
FIG. 6 is a bottom view showing a supporting means, etc.

FIGS. 3 and 4 show the syringe barrel receiving means 9 attached to the supporting means 3. The syringe barrel receiving means 9 has a hollow part 9' into which the above-mentioned end 7a of the syringe barrel 7 is inserted. The syringe barrel receiving means 9 has a cylindrical portion 33 and guide pins 35 which protrude therefrom. The cylindrical portion 33 has a cut 37 corresponding to the needle removing means 17 of the rotatable member 11. The above-mentioned portion 19 of the syringe barrel receiving means 9 is a projection formed on the syringe barrel receiving means 9.

Figure 10:
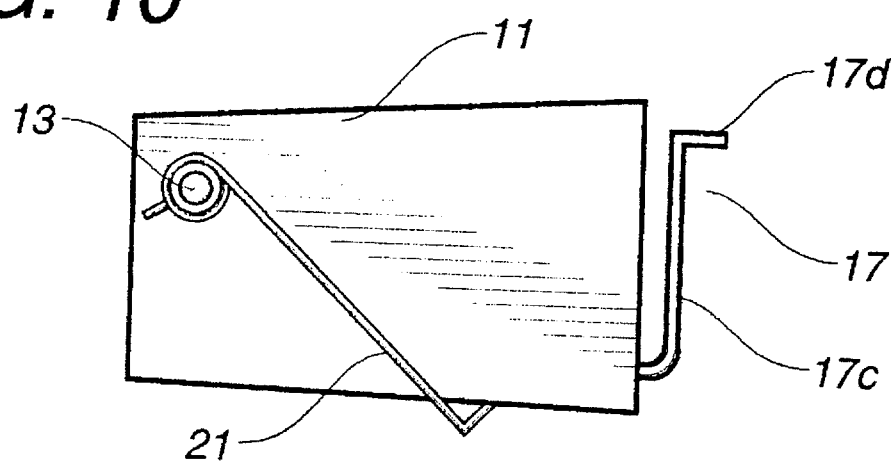
FIG. 10 is a side view showing another example of the needle removing means and a spring means.

The above-mentioned spring means 21 may be a spring of any kind as far as it can keep each of the rotatable members 11 in contact with the portion 19 of the syringe barrel receiving means 9 and return the rotatable members 11 and the syringe barrel receiving means 9 respectively to their original positions. If two rotatable members 11 are disposed, the spring means 21 may be attached between the rotatable members 11 as shown in FIGS. 1, 2 and 6 to 8. As shown in FIG. 10, the spring means 21 may be attached between each rotatable member 11 and its supporting shaft 13.

The device for removing a needle from a syringe according to the present invention has the following advantages:

A needle can be removed from a used syringe simply by pressing an end of the syringe barrel having the needle against said syringe barrel receiving means. Since the direction in which the syringe barrel is pushed is the same as the direction in which the needle is removed from the syringe, the operation of the device is very easy and smooth. The needle is removed from the syringe surely and safely.

Since the distance for which said needle removing means moves is longer than the distance for which said portion of the syringe barrel receiving means moves, the needle removing means of the rotatable member or members surely removes the needle from the syringe barrel.

Since said needle removing means of said rotatable member or members has elasticity, the needle removing means grasps the needle with a suitable force. Therefore, the needle removing means surely contacts the needle and smoothly separates the needle from the syringe barrel without damaging or destroying the needle.

The foregoing disclosure and description of the invention is illustrative and explanatory therof. Various changes in the details of the illustrated configuration can be made within the scope of the appended claims without departing from the true spirit of the invention. The present invention should only be limited by the following claims and their legal equivalents.

What is claimed is:

1. A device for removing a needle from a syringe, the needle being non-threadedly attached to the syringe, the device comprising a supporting member, a syringe barrel receiving means attached to said supporting member slidably in a direction aligned with a longitudinal axis of the syringe, a first rotatable member having a needle removing means for pushing the needle from the syringe, a second rotatable member having a needle removing means for pushing the needle from the syringe in cooperation with said needle removing means of said first rotatable member, each of said rotatable members being attached to said supporting member so as to have an axis of rotation which is transverse to the longitudinal axis of the syringe, said rotatable members further having a spring means for keeping said rotatable members in contact with a portion of said syringe barrel receiving means and for returning said rotatable members and said syringe barrel receiving means to their original positions.

2. The device for removing a needle from a syringe as claimed in claim 1, wherein a distance between a position in which said portion of said syringe barrel receiving means contacts each of said rotatable members and said axis of rotation of each of said rotatable members is shorter than a distance between said needle removing means of each of said rotatable members and said axis of rotation of each of said rotatable members.

3. The device for removing a needle from a syringe as claimed in claim 1, wherein said needle removing means of each of said rotatable members has elasticity.

4. The device for removing a needle from a syringe as claimed in claim 2, wherein said needle removing means of each of said rotatable members has elasticity.

* * * * *